(12) United States Patent
Hong

(10) Patent No.: US 11,977,066 B2
(45) Date of Patent: May 7, 2024

(54) COMBUSTION ANALYZER

(71) Applicant: Fieldpiece Instruments, Inc., Orange, CA (US)

(72) Inventor: Tinggui Hong, Orange, CA (US)

(73) Assignee: Fieldpiece Instruments, Inc., Orange, CA (US)

(*) Notice: Subject to any disclaimer, the term of this patent is extended or adjusted under 35 U.S.C. 154(b) by 627 days.

(21) Appl. No.: 16/407,807

(22) Filed: May 9, 2019

(65) Prior Publication Data

US 2019/0360985 A1 Nov. 28, 2019

Related U.S. Application Data

(60) Provisional application No. 62/676,804, filed on May 25, 2018.

(51) Int. Cl.
*G01N 33/00* (2006.01)
*G01N 27/409* (2006.01)

(52) U.S. Cl.
CPC ....... *G01N 33/0073* (2013.01); *G01N 27/409* (2013.01); *G01N 33/0013* (2013.01); *G01N 33/0032* (2013.01)

(58) Field of Classification Search
None
See application file for complete search history.

(56) References Cited

U.S. PATENT DOCUMENTS

| | | | | |
|---|---|---|---|---|
| 5,055,266 A | * | 10/1991 | Stetter | G01N 33/0032 436/120 |
| 5,205,177 A | * | 4/1993 | DuBrock, Jr. | G01N 33/0016 73/863.12 |
| 7,588,726 B1 | * | 9/2009 | Mouradian | G01N 33/0009 702/22 |
| 9,846,107 B1 | | 12/2017 | D'Amico et al. | |
| 10,837,877 B2 | * | 11/2020 | Siperstein | G01N 1/2214 |
| 2003/0110993 A1 | | 6/2003 | Slater et al. | |
| 2012/0245878 A1 | * | 9/2012 | Kane | G05B 15/02 702/116 |
| 2014/0193922 A1 | | 7/2014 | Alberti et al. | |
| 2014/0250975 A1 | * | 9/2014 | Kane | G01N 1/2205 73/23.31 |
| 2015/0355150 A1 | | 12/2015 | Ikezawa et al. | |
| 2016/0061799 A1 | | 3/2016 | Epperson | |

FOREIGN PATENT DOCUMENTS

DE 19855831 A1 * 3/2000 ........... G01N 27/407

OTHER PUBLICATIONS

International Search Report and Written Opinion dated Aug. 28, 2019 from IA No. PCT/US2019/031528.

* cited by examiner

*Primary Examiner* — Daniel S Larkin
(74) *Attorney, Agent, or Firm* — Paul J. Backofen, Esq.

(57) ABSTRACT

A combustion analyzer system includes an analyzer unit, a primary analysis probe and one or more remote probes. The analyzer unit includes a condensation removal unit and two or more electrochemical sensors to detect at least oxygen and carbon monoxide. The analyzer unit also includes a means for sealing or isolating the electrochemical sensor inputs to prevent oxidation of the reactive elements when the unit is not in use.

14 Claims, 7 Drawing Sheets

COMBUSTION ANALYZER

This application claims priority to U.S. Provisional Application 62/676,804, filed May 25, 2018.

FIELD OF THE INVENTIONS

The inventions described below relate to the field of combustion analyzers

BACKGROUND OF THE INVENTIONS

Conventional combustion analyzers include a water trap to collect condensed liquid from the stream of combustion by-products. The condensed liquid also contains many combustion by-products creating a toxic soup that must be disposed in a specific manner when the trap reaches capacity. In addition, the water traps are susceptible to freeze induced breakage if left full in low temperatures.

Many of the electrochemical sensor elements in conventional combustion analyzers contain liquid electrolyte and other elements that are highly reactive with oxygen. The flue gasses that the sensor elements are exposed to have a low percentage of free oxygen. However, when the combustion analyzer is not in use, the electrochemical sensors are exposed to air with about 21% oxygen. Consequently, the reactive elements of the electrochemical sensors are rapidly consumed and the electrolyte either dries out in low humidity or is diluted by attracting water in high humidity environments.

SUMMARY

The devices and methods described below provide for a combustion analyzer system that avoids the problems of collecting and disposing of hazardous condensate and preserves the reactive elements in the sensors when the system is not in use. The combustion analyzer system has an analyzer unit, a primary analysis probe and optional remote probes. The analyzer unit includes a condensation elimination unit and one or more electrochemical sensors to detect, for example, oxygen and carbon monoxide. The condensation elimination unit is operable to separate condensable vapors in the flue gas, or moisture in the flue gas, or both. Dry flue gas is directed to the sensor(s), and the condensed vapors or separated moisture is directed to a mister for dispersal or directed back into the flue for dispersal in the flue.

In an alternate configuration a primary analysis probe includes a secondary controller, a condenser/moisture separator and fan to cool and separate the combustion gas from the condensable liquid to return the liquid from the gas stream to the probe tip as liquid for injection into the flue. The primary analysis probe also includes temperature and pressure sensors in the probe tip. The analyzer unit includes two or more electrochemical sensors to detect at least oxygen and carbon monoxide and the primary controller. The analyzer unit also includes a means for sealing or isolating the electrochemical sensor inputs to prevent oxidation of the reactive elements and preserve the electrolyte when the unit is not in use.

DETAILED DESCRIPTION OF THE INVENTIONS

Figure 1:
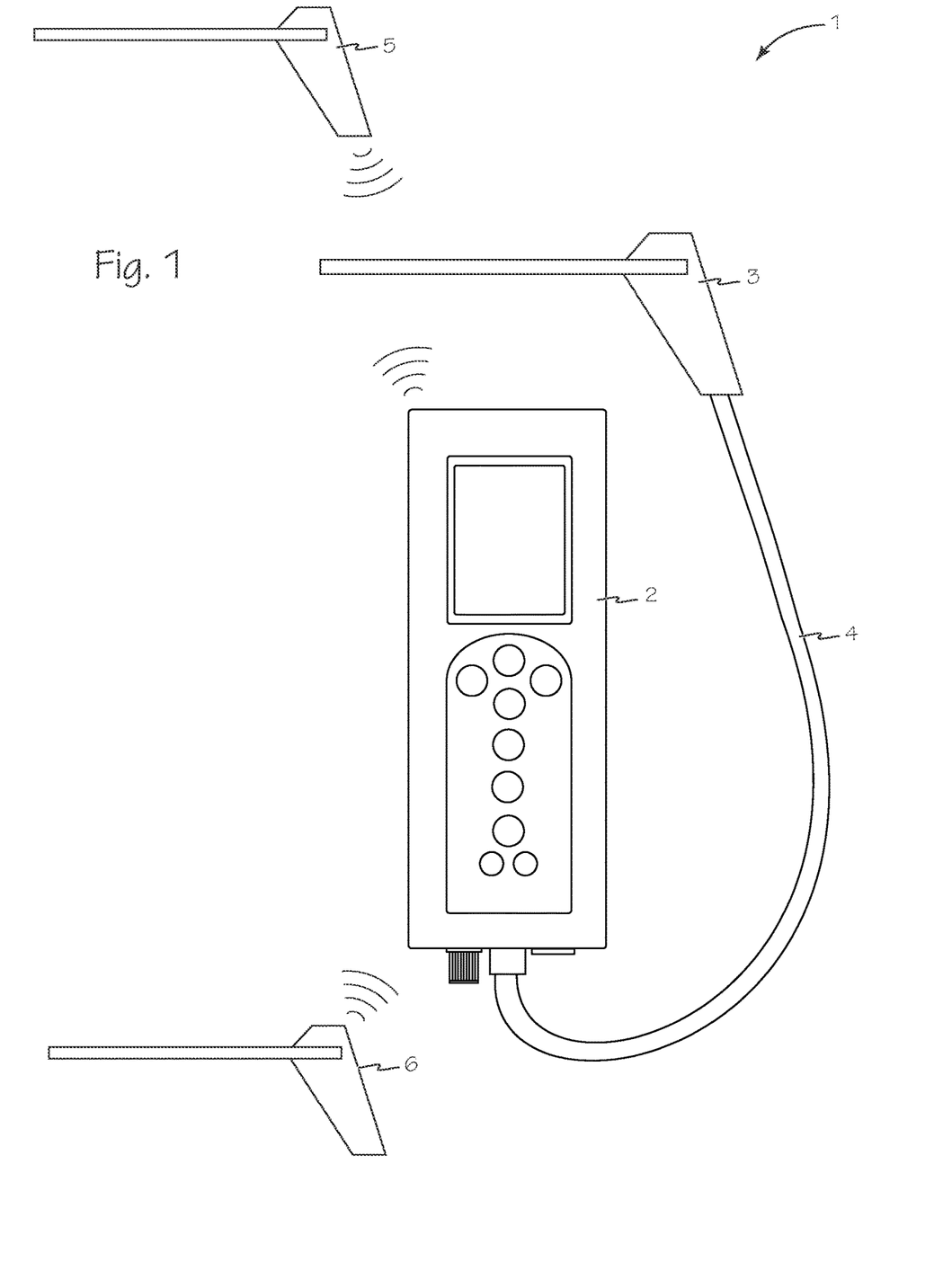
FIG. 1 is an illustration of a combustion analyzer system.

FIG. 1 is an illustration of combustion analyzer system 1. The combustion analyzer system 1 includes an analyzer unit 2 which is operatively connected to primary probe 3 via cable 4. One or more optional remote probes, such as probes 5 and 6, may communicate with analyzer unit 2 using any suitable technique.

Figure 2:
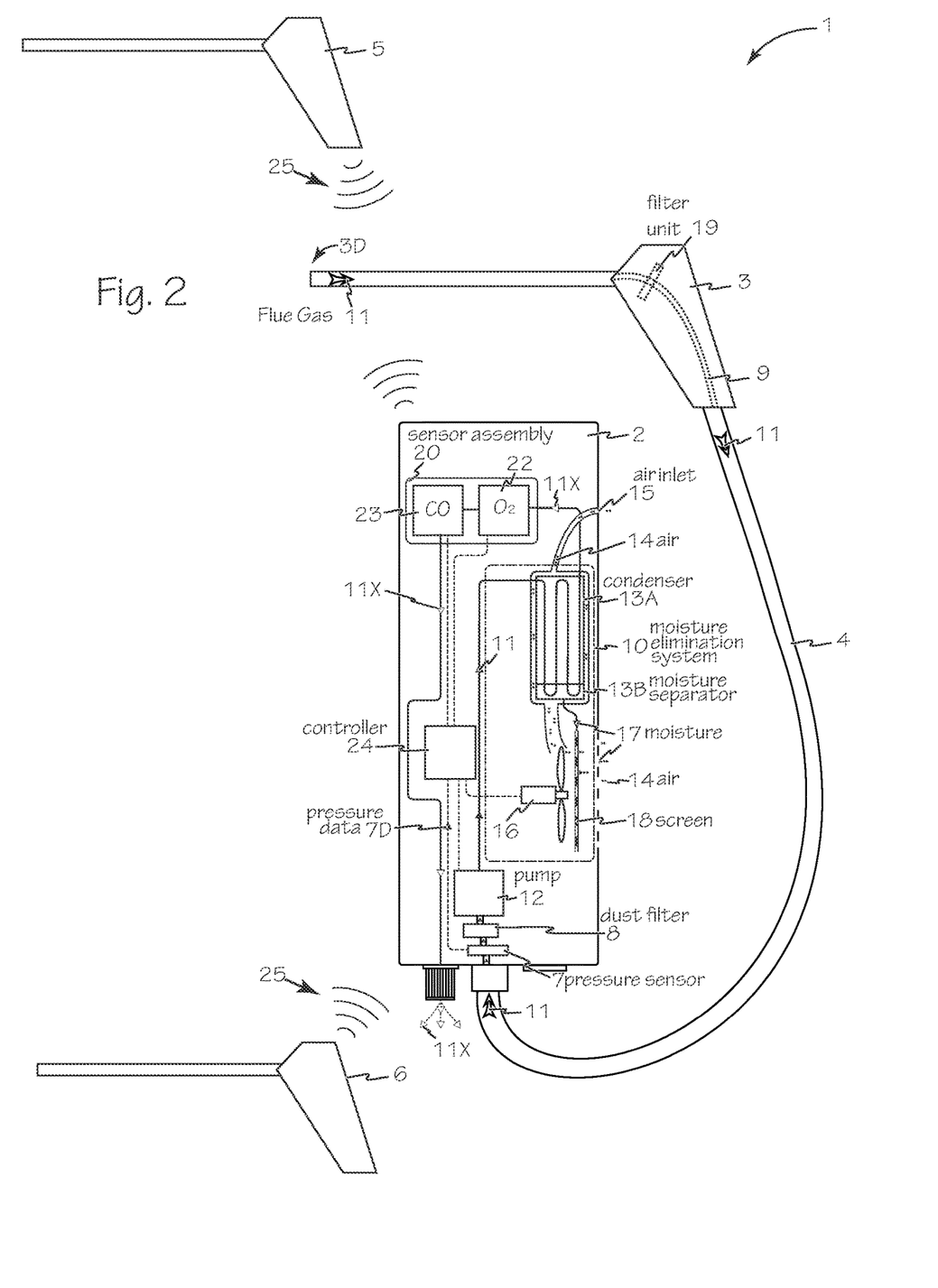
FIG. 2 is an illustration of some of the internal components of the combustion analyzer of FIG. 1.

The combustion analyzer unit 2 illustrated in FIG. 1 is shown in FIG. 2 with some of the internal components illustrated. The combustion analyzer unit 2 includes a condensation elimination system 10 that does not require emptying a liquid trap. Flue gas or combustion by-products or combustion gas 11 is drawn into the analyzer unit 2 through an optional secondary filter, such as dust filter 8, by a pump 12. The flue gas is pumped into condenser 13A where the condensable gasses in the flue gas are condensed to liquid and separated from the flue gas by the relatively cool ambient air 14 being drawn from air inlet 15 and circulated around and through the condenser by fan 16. The condensation elimination system may also comprise a moisture separator, either in lieu of or in addition to the condenser, which operates to separate moisture from the flue gas. The condensed liquid, condensate 17, or moisture from the moisture separator, is separated from the flue gas and the condensate/moisture from the separator is conducted to any suitable atomizer, such as screen or net 18, where it is exhausted from the analyzer unit 2 with the ambient air 14. The screen serves to atomize or aerosolize the condensate or moisture from the separator. Any other suitable technique for aerosolizing the condensate/moisture from the separator may also be used, such as a mist generator or misting nozzle. The acid content of the separated moisture may be minimized by the use of filter unit 19 (a ceramic catalyst filter for example) in primary probe 3 to filter the NOx and the SOx out of flue gas 11. Dust filter 8 and the filter unit 19 may be located together or separately in the primary probe or the analyzer unit.

The filtered, dry flue gas 11X is moved from the condenser/moisture separator 13 into a sensor assembly 20, by pump 12. In sensor assembly 20, one or more electrochemical sensors, such as oxygen sensor 22 and CO sensor 23, are exposed to dry filtered flue gas 11X and each sensor produces an electrical signal corresponding to the level of their respective compound that is present in the dry, filtered flue gas 11X. The electrochemical sensors in sensor assembly 20 are operatively connected to controller 24, which analyzes the electrical signals from the electrochemical sensors and produces an output signal corresponding to the measured characteristics of dry, filtered flue gas 11X. The controller 24 includes one or more microprocessors and is operatively connected to the fan, the pump, the primary probe, the sensors and another components capturing data or providing feedback to a user. The controller is operable to turn the fan on when liquid is present in the moisture separator.

Tube 9 inside the hose/cable 4 conducts the flue gas 11 to a gas pressure sensor 7 in the analyzer unit 2, which enables the pressure sensor to detect the draft pressure of the flue. A stable pressure sensor (maintains accuracy for about 30 minutes) and the analyzer unit may be used monitor the draft pressure and provide the pressure data 7D to the controller for display to a user.

Optional remote probes 5 and 6 measure chemical, thermal and other characteristics of a combustion system, such as flue pressure, and these characteristics are transmitted as signals 25 to controller 24 and may be displayed on the analyzer unit and/or any suitable mobile device.

Figure 3:
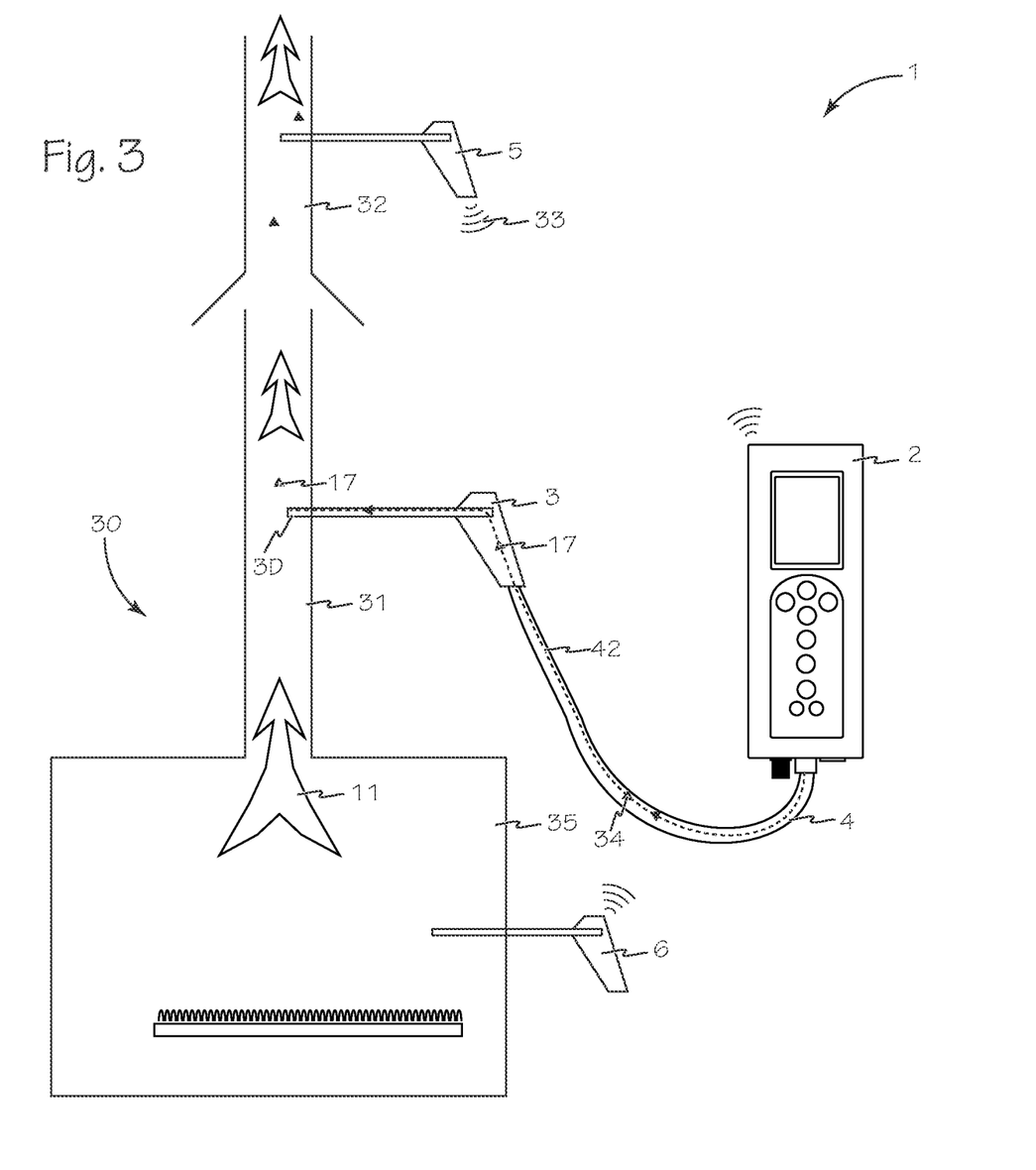
FIG. 3 illustrates the use of the combustion analyzer of FIG. 1 in an installed heating system.

FIG. 3 illustrates the use of the combustion analyzer of FIG. 1 in combustion system 30. In use, analyzer unit 2 is connected to primary probe 3 and distal end 3D is inserted into the primary system flue 31. Remote probe 5 is inserted into secondary system flue 32 to provide reference data 33 to compare to primary data 34 from the primary probe 3. Reference data 33 may include flue pressure, temperature, humidity/relative humidity and air flow rate. Firebox measurements may be accomplished by using a remote probe, such as probes 5 or 6 inserted into firebox 35.

Figure 4:
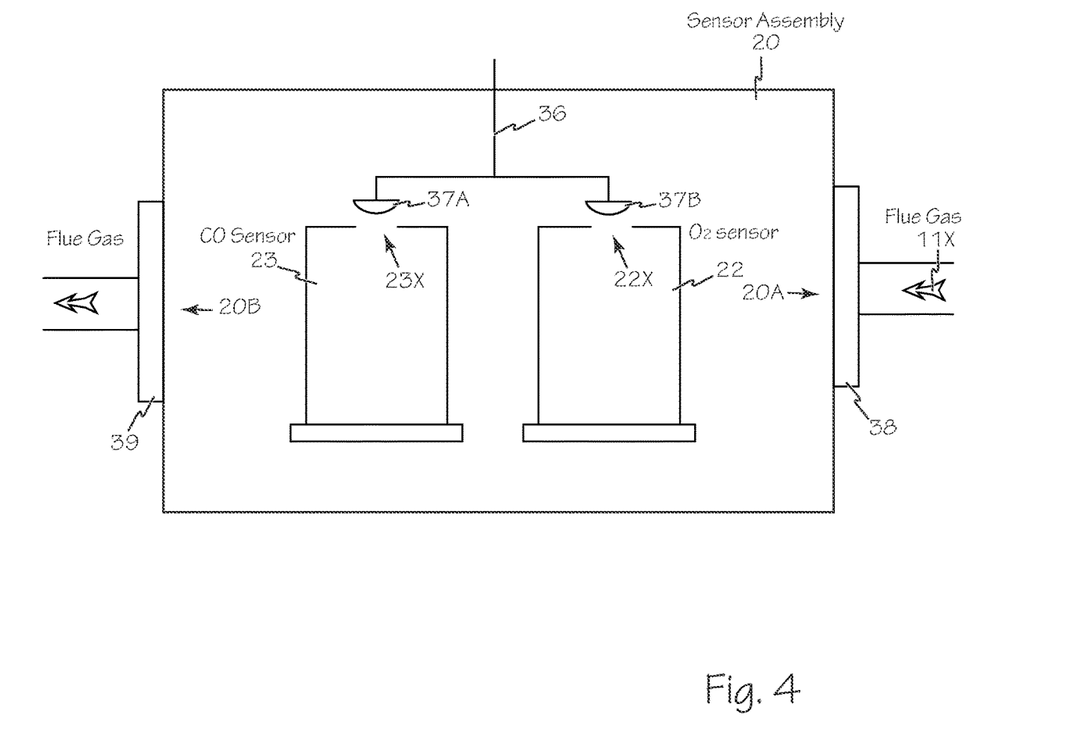
FIG. 4 is a close up illustration of the sensor assembly of the combustion analyzer of FIG. 1.

FIG. 4 is a close up illustration of sensor assembly 20. Sensor sealer 36 is a plunger that applies any suitable sealing element to each sensor orifice. Sealing element 37A seals electrochemical sensor orifice 23X and sealing element 37B seals electrochemical sensor orifice 22X. One or more optional moisture filters, such as moisture filters 38 and 39, may be provided at gas input 20A and gas output 20B respectively.

Figure 5:
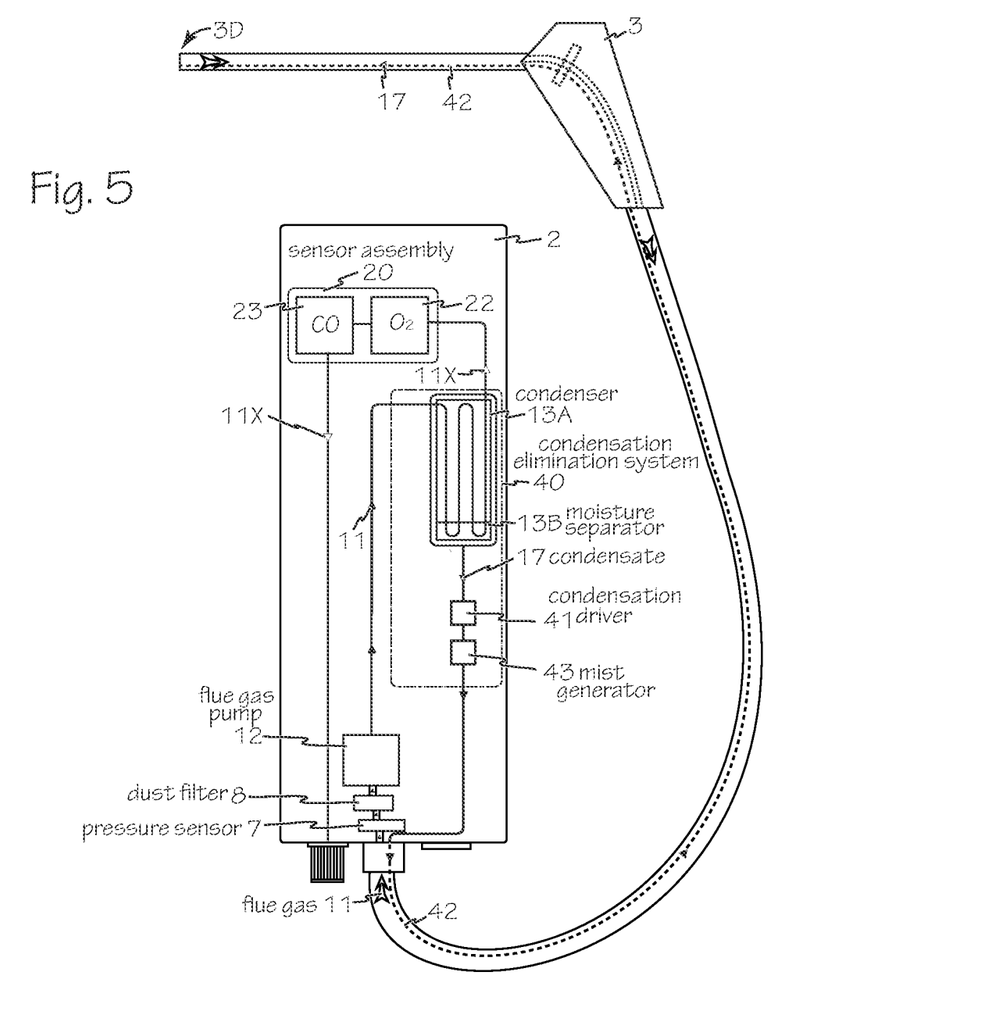
FIG. 5 is an illustration of the combustion analyzer system of FIG. 1 with an alternate condensation system.

The condensation system 40 of FIG. 5 removes moisture from the flue gas to be tested and returns the moisture as condensate 17 to the primary system flue via condensate driver 41 and condensate return line 42 which conducts the condensate from the condensation system to the distal end 3D of the primary probe 3 and back into the primary flue 31, as illustrated in FIG. 3. The condensation driver 41 may be any suitable fan or pump. An optional mist generator 43 may use any suitable technology, such as a piezo inducer, to reduce condensate to a mist for conduction and reintroduction into the primary flue. The optional mist generator 43 may also be used in place of the metal screen or net 18.

Figure 6:
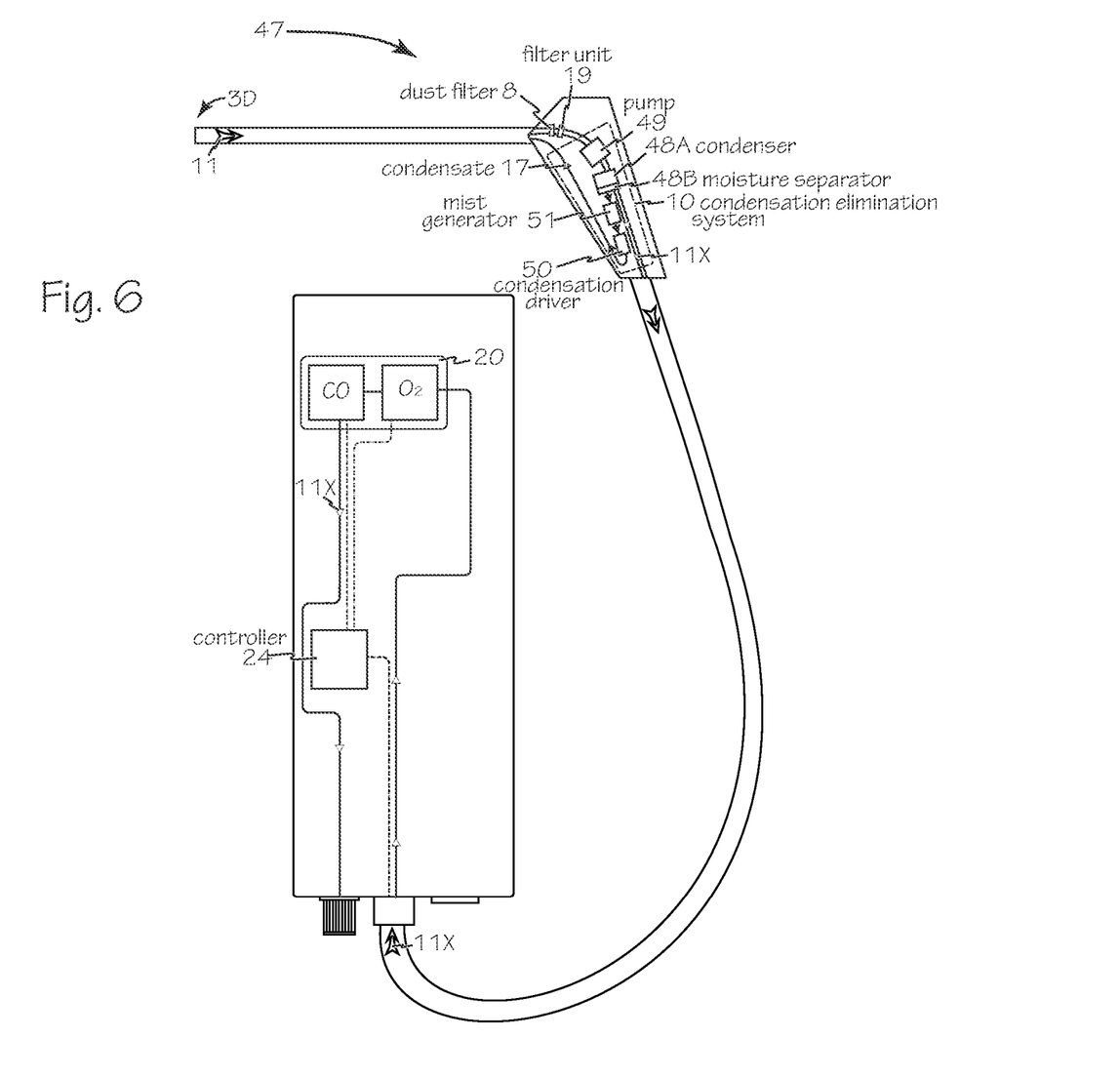
FIG. 6 is an illustration of the combustion analyzer system of FIG. 1 with the condensation system in the primary probe.

FIG. 6 is an illustration of the combustion analyzer system of FIG. 1 with the condensation system 10 in the primary probe 47. Flue gas 11 is drawn into the primary probe where it is filtered as discussed above and is then pumped into condenser 48A and then moisture separator 48B by any suitable pump, such as pump 49. The dry, filtered flue gas 11X is then conducted to the sensor assembly 20 for testing as discussed above. Condensate 17 is pumped from the moisture separator 48 using any suitable condensation driver such as pump 50. Optional mist generator 51 may also be used to reduce the condensate to a mist for conduction and reintroduction into the primary flue.

Figure 7:
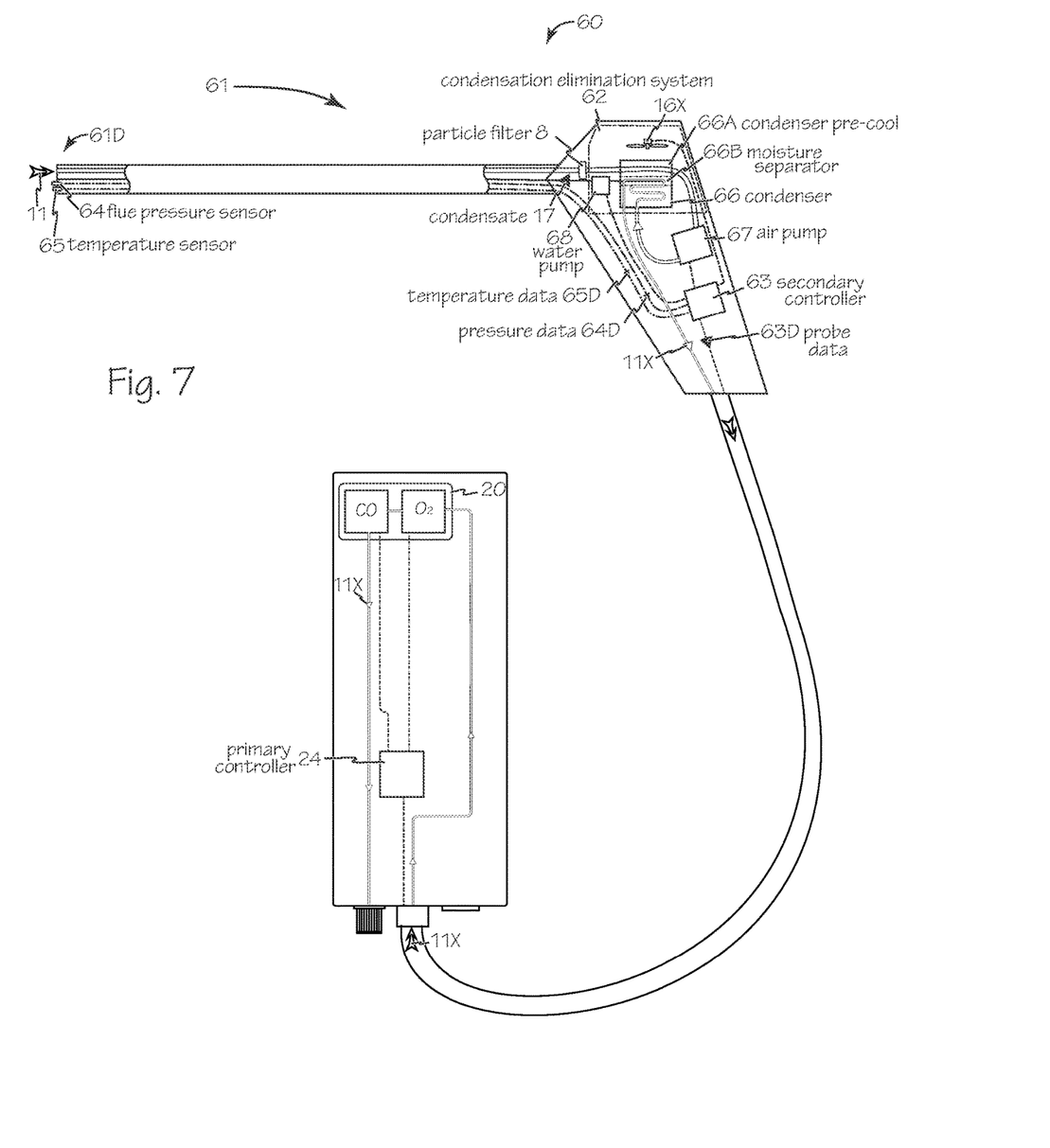
FIG. 7 is an illustration of an alternate combustion analyzer with the moisture separator and secondary controller in the probe and the primary controller in the analyzer unit.

Alternate combustion analyzer system 60 is illustrated in FIG. 7. System 60 includes primary probe 61 which houses the condensation elimination system 62, a secondary controller 63, as well as the optional flue pressure sensor 64 and the optional temperature sensor 65. Pressure data 64D and temperature data 65D may be collected by the secondary controller 63 and combined with other probe data and are forwarded to the primary controller 24 as probe data 63D for display to the user and transmission to other devices. Flue gas 11 is drawn into the primary probe 61 where it is filtered as discussed above and is then drawn through the moisture separator pre-cool chamber 66A by any suitable pump, such as air pump 67, and then through the moisture separator 66B. Fan 16X is operably connected to secondary controller 63. The dry, filtered flue gas 11X is then conducted to the sensor assembly 20 for testing as discussed above. Condensate 17 is pumped from the moisture separator 66B out through the distal end 61D of the primary probe using any suitable condensation driver, such as water pump 68.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A combustion analyzer system comprising:
   a combustion analyzer unit having one or more electrochemical sensors;
   a primary probe having a distal end and a condensation elimination system operably connected to the combustion analyzer unit, the primary probe operable to conduct combustion by-products to the one or more electrochemical sensors;
   a primary controller operatively connected to the combustion analyzer unit and the primary probe;
   one or more secondary probes operable to communicate with the combustion analyzer unit; and
   a sensor sealer in the combustion analyzer unit operatively connected to the one or more electrochemical sensors to seal the one or more electrochemical sensors when not in use.

2. The combustion analyzer system of claim 1 wherein the primary probe further comprises a secondary controller operatively connected to the primary controller.

3. The combustion analyzer system of claim 2 wherein the secondary controller is operably connected to a fan to turn the fan on when liquid is present in the condensation elimination system.

4. The combustion analyzer system of claim 2 wherein the primary probe further comprises:
   a pressure sensor operably connected to the secondary controller.

5. The combustion analyzer system of claim 2 wherein the primary probe further comprises:
   a temperature sensor operably connected to the secondary controller.

6. The combustion analyzer system of claim 2 wherein the primary probe further comprises:
   a pressure sensor and a temperature sensor wherein the sensors are operably connected to the secondary controller.

7. The combustion analyzer system of claim 1 wherein the condensation elimination system comprises:
   a condenser operably connected to receive combustion by-products within the primary probe and condense and separate any liquid from the combustion gas into condensate;
   a return line operatively connected between the condenser and the distal end of the primary probe; and
   a pump operable to pump the condensate through the return line to be ejected from the distal end of the primary probe.

8. The combustion analyzer system of claim 7 wherein the condenser further comprises a pre-cooler.

9. The combustion analyzer system of claim 7 wherein the secondary controller is operably connected to a fan to turn the fan on when liquid is present in the condenser.

10. The combustion analyzer system of claim 1 wherein the condensation elimination system comprises:
   a moisture separator operably connected to receive combustion by-products within the primary probe and separate any liquid from the combustion gas into condensate;
   a return line operatively connected between the moisture separator and the distal end of the primary probe; and
   a pump operable to pump the condensate through the return line to be ejected from the distal end of the primary probe.

11. The combustion analyzer system of claim 10 wherein the moisture separator further comprises a pre-cooler.

12. The combustion analyzer system of claim 10 wherein the secondary controller is operably connected to a fan to turn the fan on when liquid is present in the moisture separator.

13. A combustion analyzer system comprising:
   a combustion analyzer unit having one or more electrochemical sensors operably connected to a primary controller;
   a primary probe having a condensation elimination system, a pressure sensor, a temperature sensor and a secondary controller operably connected to the primary controller, the primary probe operable to conduct combustion by-products to the one or more electrochemical sensors;
   one or more secondary probes operable to communicate with the primary controller; and
   a sensor sealer in the combustion analyzer unit operatively connected to the one or more electrochemical sensors to seal the one or more electrochemical sensors when not in use.

14. A method of collecting flue gas for analysis and disposing of condensate from the flue gas comprising the steps:
   collecting flue gas from an active flue;
   drying the flue gas by condensing condensable vapors in the flue gas, thereby creating a stream of flue gas which can be passed to a sensor and a collection of condensates or collected moisture;
   disposing of the collection of condensates or collected moisture by directing the collection of condensates or collected moisture into the active flue; and
   conducting the dry flue gas to the sensor operable to detect a constituent of the flue gas.

* * * * *